(12) United States Patent
Mueller

(10) Patent No.: US 7,211,041 B2
(45) Date of Patent: May 1, 2007

(54) APPARATUS AND METHOD FOR DELIVERING THERAPEUTIC AND DIAGNOSTIC AGENTS

(75) Inventor: Richard Mueller, Byron, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 36 days.

(21) Appl. No.: 11/090,859

(22) Filed: Mar. 25, 2005

(65) Prior Publication Data

US 2005/0171474 A1  Aug. 4, 2005

Related U.S. Application Data

(63) Continuation of application No. 10/370,646, filed on Feb. 20, 2003, now abandoned, which is a continuation of application No. 09/566,196, filed on May 5, 2000, now Pat. No. 6,565,528.

(60) Provisional application No. 60/133,179, filed on May 7, 1999.

(51) Int. Cl.
*A61B 1/00* (2006.01)
(52) U.S. Cl. .......................... 600/106; 606/41; 600/459
(58) Field of Classification Search ..................... None
See application file for complete search history.

(56) References Cited

U.S. PATENT DOCUMENTS

| | | |
|---|---|---|
| 2,491,978 A | 12/1949 | Helfman et al. |
| 3,057,349 A | 10/1962 | Ismach |
| 3,773,034 A | 11/1973 | Burns et al. |
| 3,859,996 A | 1/1975 | Mizzy et al. |
| 3,952,742 A | 4/1976 | Taylor |
| 4,171,852 A | 10/1979 | Haentjens |
| 4,243,035 A | 1/1981 | Barrett |
| 4,266,541 A | 5/1981 | Landau |
| 4,296,100 A | 10/1981 | Franco |
| 4,447,225 A | 5/1984 | Taff et al. |
| 4,531,936 A | 7/1985 | Gordon |
| 4,576,591 A | 3/1986 | Kaye et al. |
| 4,657,536 A | 4/1987 | Dorman |
| 4,680,027 A | 7/1987 | Parsons et al. |

(Continued)

FOREIGN PATENT DOCUMENTS

EP    0 489496 A1    6/1992

(Continued)

OTHER PUBLICATIONS

Boretos, J.W., "Improved intravascular delivery of drug via a polyethylene jet catheter" *13th Annual Meeting of the Society for Biomaterials*, Jun. 2-6 pp. 128 (1987).

(Continued)

*Primary Examiner*—Thor Campbell
(74) *Attorney, Agent, or Firm*—Jones Day

(57) ABSTRACT

A drug-delivery tool and method for delivering a diagnostic or therapeutic agent to a target site within a selected body tissue, such as the myocardium of the heart, is disclosed. The drug-delivery tool generally includes an accessing device having a tissue-penetrating implement in its distal-end region, and elements for delivering a selected agent into a cavity formed by the implement. Methods of use are also described.

17 Claims, 12 Drawing Sheets

U.S. PATENT DOCUMENTS

| | | | |
|---|---|---|---|
| 4,770,653 A | 9/1988 | Shturman | |
| 4,838,850 A | 6/1989 | Rosengart | |
| 4,861,339 A | 8/1989 | Jonischkeit | |
| 4,911,148 A | 3/1990 | Sosnowski et al. | |
| 4,946,442 A | 8/1990 | Sanagi | |
| 4,994,033 A | 2/1991 | Shockey et al. | |
| 5,034,003 A | 7/1991 | Denance | |
| 5,061,273 A | 10/1991 | Yock | |
| 5,100,792 A | 3/1992 | Sanford et al. | |
| 5,106,370 A | 4/1992 | Stewart | |
| 5,114,423 A | 5/1992 | Kasprzyk et al. | |
| 5,130,141 A | 7/1992 | Law et al. | |
| 5,179,022 A | 1/1993 | Sanford et al. | |
| 5,185,004 A | 2/1993 | Lashinski | |
| 5,197,946 A | 3/1993 | Tachibana | |
| 5,203,772 A | 4/1993 | Hammerslag et al. | |
| 5,228,883 A | 7/1993 | Blakely et al. | |
| 5,244,460 A | 9/1993 | Unger et al. | |
| 5,307,803 A | 5/1994 | Matsuura et al. | |
| 5,308,324 A | 5/1994 | Hammerslag et al. | |
| 5,322,511 A | 6/1994 | Armbruster et al. | |
| 5,328,470 A | 7/1994 | Nabel et al. | |
| 5,336,178 A | 8/1994 | Kaplan et al. | |
| 5,356,388 A | 10/1994 | Sepetka et al. | |
| 5,370,685 A | 12/1994 | Stevens | |
| 5,372,587 A | 12/1994 | Hammerslag et al. | |
| 5,380,279 A | 1/1995 | Schmidt | |
| 5,389,096 A | 2/1995 | Aita et al. | |
| 5,395,312 A | 3/1995 | Desai | |
| 5,429,131 A | 7/1995 | Scheinman et al. | |
| 5,431,168 A | 7/1995 | Webster, Jr. | |
| 5,476,100 A | 12/1995 | Galel | |
| 5,480,381 A | 1/1996 | Weston | |
| 5,480,382 A | 1/1996 | Hammerslag et al. | |
| 5,492,119 A | 2/1996 | Abrams | |
| 5,499,971 A | 3/1996 | Shapland et al. | |
| 5,507,724 A | 4/1996 | Hofmann et al. | |
| 5,569,160 A | 10/1996 | Sauer et al. | |
| 5,569,217 A | 10/1996 | Luther | |
| 5,580,859 A | 12/1996 | Felgner et al. | |
| 5,591,195 A | 1/1997 | Taheri et al. | |
| 5,630,795 A | 5/1997 | Kuramoto et al. | |
| 5,642,730 A | 7/1997 | Baran | |
| 5,652,225 A | 7/1997 | Isner | |
| 5,653,684 A | 8/1997 | Laptewicz et al. | |
| 5,661,133 A | 8/1997 | Leiden et al. | |
| 5,698,531 A | 12/1997 | Nabel et al. | |
| 5,707,969 A | 1/1998 | Nabel et al. | |
| 5,725,523 A | 3/1998 | Mueller | |
| 5,739,118 A | 4/1998 | Carrano et al. | |
| 5,760,081 A | 6/1998 | Leaf et al. | |
| 5,772,590 A | 6/1998 | Webster, Jr. | |
| 5,782,239 A | 7/1998 | Webster, Jr. | |
| 5,782,802 A | 7/1998 | Landau | |
| 5,792,453 A | 8/1998 | Hammond et al. | |
| 5,797,870 A | 8/1998 | March et al. | |
| 5,803,083 A | 9/1998 | Buck et al. | |
| 5,807,306 A | 9/1998 | Shapland et al. | |
| 5,820,592 A | 10/1998 | Hammerslag | |
| 5,827,216 A | 10/1998 | Igo et al. | |
| 5,833,658 A | 11/1998 | Levy et al. | |
| 5,836,905 A | 11/1998 | Lemelson et al. | |
| 5,837,533 A | 11/1998 | Boutin | |
| 5,840,031 A | 11/1998 | Crowley | |
| 5,840,059 A | 11/1998 | March et al. | |
| 5,840,062 A | 11/1998 | Gumaste et al. | |
| 5,843,050 A | 12/1998 | Jones et al. | |
| 5,846,221 A | 12/1998 | Snoke et al. | |
| 5,846,225 A | 12/1998 | Rosengart et al. | |
| 5,854,209 A | 12/1998 | Jacobs, Jr. et al. | |
| 5,857,464 A | 1/1999 | Desai | |
| 5,860,953 A | 1/1999 | Snoke et al. | |
| 5,865,811 A | 2/1999 | Doying, Sr. et al. | |
| 5,871,462 A | 2/1999 | Yoder et al. | |
| 5,871,495 A | 2/1999 | Mueller | |
| 5,876,373 A | 3/1999 | Giba et al. | |
| 5,882,332 A | 3/1999 | Wijay | |
| 5,885,272 A | 3/1999 | Aita et al. | |
| 5,891,086 A | 4/1999 | Weston | |
| 5,891,136 A | 4/1999 | McGee et al. | |
| 5,935,063 A | 8/1999 | Nguyen | |
| 5,941,868 A | 8/1999 | Kaplan et al. | |
| 5,951,516 A | 9/1999 | Bunyan | |
| 5,971,983 A | 10/1999 | Lesh | |
| 5,993,443 A | 11/1999 | Murphy-Chutorian et al. | |
| 5,997,509 A | 12/1999 | Rosengart et al. | |
| 6,004,269 A | 12/1999 | Crowley et al. | |
| 6,006,123 A | 12/1999 | Nguyen et al. | |
| 6,007,531 A | 12/1999 | Snoke et al. | |
| 6,017,322 A | 1/2000 | Snoke et al. | |
| 6,024,703 A | 2/2000 | Zanelli et al. | |
| 6,036,677 A | 3/2000 | Javier, Jr. et al. | |
| 6,056,742 A | 5/2000 | Murphy-Chutorian et al. | |
| 6,102,887 A | 8/2000 | Altman | |
| 6,224,566 B1 * | 5/2001 | Loeb | 604/22 |
| 6,309,370 B1 * | 10/2001 | Haim et al. | 604/66 |

FOREIGN PATENT DOCUMENTS

| | | |
|---|---|---|
| WO | WO 92/10142 | 6/1992 |
| WO | WO 94/21237 | 9/1994 |
| WO | WO 94/24263 | 10/1994 |
| WO | WO 97/17099 | 5/1997 |
| WO | WO 97/36633 | 10/1997 |
| WO | WO 97/42998 | 11/1997 |
| WO | WO 97/49450 | 12/1997 |
| WO | WO 98/05307 | 2/1998 |
| WO | WO 98/10750 | 3/1998 |
| WO | WO 98/31409 | 7/1998 |
| WO | WO 98/34657 | 8/1998 |
| WO | WO 98/57695 | 12/1998 |
| WO | WO 98/57696 | 12/1998 |
| WO | WO 99/04704 | 4/1999 |
| WO | WO 00/02612 | 1/2000 |

OTHER PUBLICATIONS

Newman, J.H., and Ross, J.C., "Primary pulmonary Hypertension: A Look at the Future" *JACC* 14(3):551-555 (1989).

Schmacher, B., et al., "Induction of Neoangiogenesis in Ischemic Myocardium by Human Growth Factors" *Circulation* 97:645-650 (1998).

Seldinger, S.I., "Catheter replacement of the needle in percutaneous arteriography" *Acta Radiologica* 39:368-376 (1953).

"TDMAC-Heparin Complex", Data Sheet #172, Apr. 2000.

Amiji et al., "Surface modification of polymeric biomaterials with poly(ethylene oxide), albumin, and heparin for reduced thrombogenicity", *J. Biomater, Sci. Polymer Edn.*, vol. 4, No. 3, pp. 217-234 (1993).

von Segesser, Ludwig K., "Heparin-Bonded Surfaces in Extracorporeal Membrane Oxygenation of Cardiac Support", http://ats.ctsnetjournals.org/cgi/content/full/61/1/330 (1996).

Hubbell, Jeffrey A., "Pharmacologic Modification of Materials", *Cardiovasc Pathol*, vol. 2, No. 3 (Suppl.) Jul.-Sep. 1993:121S-127S.

Helmus et al., "Medical Device Design—A Systems Approach: Central Venous Catheters", 22$^{nd}$ *International SAMPE Technical Conference*, Nov. 6-8, pp. 113-126 (1990).

Peng et al., "Role of polymers in improving the results of stenting in coronary arteries", *Biomaterials*, vol. 17, No. 7. pp. 685-694 (1996).

Horrow, "Heparin-Coated Cardiopulmonary Bypass Circuits", *Journal of Cardiothoracic and Vascular Anesthesia*, vol. 8, No. 2 (April), pp. 213-222 (1994).

Ishihara et al., "Synthesis of phospholipid polymers having a urethane bond in the side chain as coating material on segmented polyurethane and their platelet adhesion-resistant properties", *Biomaterials*, vol. 16, No. 11, pp. 873-879 (1995).

Sanchez et al., "Control of contact activation on end-point immobilized heparin: The role of antithrombin and the specific antithrombin-binding sequence", *Journal of Biomedical Materials Research*, vol. 29, pp. 655-661 (1995).

Barbucci, Rolando, "Coating of commercially available materials with a new heparinizable materials", *Journal of Biomedical Materials Research*, vol. 25, pp. 1259-1274 (1991).

Dennis E., Chenoweth, "Complement Activation in Extracorporeal Circuits", *Annals Of The New York Academy Of Sciences*, vol. 516, pp. 306-313 (1987).

Tong et al. "Non-thrombogenic Hemofiltration System for Acute Renal Failure Treatment", *ASAIO Journal*, pp. M702-M706 (1992).

Toomasian et al. "Evaluation of Duraflo II Heparin Coating in Prolonged Extracorporeal Membrane Oxygenation", *Trans Am Soc Artif Intern Organs*, vol. XXXIV, pp. 410-414 (1988).

Hsu, Li-Chien, "Principles of heparin-coating techniques", *Perfusion*, vol. 6, pp. 209-219 (1991).

Bergstrom et al., Reduction of fibrinogen adsorption on PEG-coated polystyrene surfaces, *Journal of Biomedical Materials Research*, vol. 26, pp. 779-790 (1992).

* cited by examiner

APPARATUS AND METHOD FOR DELIVERING THERAPEUTIC AND DIAGNOSTIC AGENTS

CROSS-REFERENCE TO RELATED APPLICATIONS

This application is a continuation of U.S. patent application Ser. No. 10/370,646 filed Feb. 20, 2003, now abandoned which is a continuation application of U.S. patent application Ser. No. 09/566,196 filed May 5, 2000, now U.S. Pat. No. 6,565,528 which claims benefit of U.S. Provisional Patent Application No. 60/133,179 filed May 7, 1999, all of which are incorporated herein by reference in their entirety.

FIELD OF THE INVENTION

The present invention is directed to an drug-delivery tool and method of delivering selected therapeutic and/or diagnostic agents to target sites in selected body tissues. More particularly, the invention provides for the creation of temporary cavities in desired layers of a selected tissue, for example, myocardial tissue of the heart, and for the delivery of one or more selected agents therein.

BACKGROUND OF THE INVENTION

Intra-muscular needle injection of therapeutic compounds is well known in the medical arts, as is intra-coronary injection where pre-existing intra-coronary arteries provide perfusate conduits. In heart disease, the existing coronary artery in-flows to capillary beds is often compromised. Newly developed gene and protein therapeutic agents hold promise in their ability to act on the surviving smaller capillary beds to grow and expand them. As has been witnessed, the intra-myocardial cellular lattice limits angiogenic response to about 5–10 mm and similar limits occur with direct needle injections in stunned or ischemid heart tissue. The physician must work within an environment of compromised capillary bed vascularity. Physicians are further limited to some degree by drug viscosity—where the drug viscosity is too-low, rapid wash-out can occur; and where too high, capillary occlusion can occur—as well as by high infusate pressure induced cellular damages. These problems are not typical of common healthy muscle tissue injections in the arm or leg. The prior art teaches the creation of permanent channels with the use of lasers, radio frequency heating and mechanical cutting means. Such channels often compromise the capillaries that are sought to be accessed with a drug, wash out readily, and resolve ultimately as fibrous connective scar tissue. Needle and membrane tools may improve access to capillaries but offer no stretching forces and don't offer unobstructed capillary access.

SUMMARY OF THE INVENTION

One embodiment of the invention provides a drug-delivery tool for delivering a drug to an internal member of a tissue, such as a heart-wall. The tool comprises an accessing device having distal and proximal ends, an inner lumen extending therebetween, a drug-delivery reservoir adapted to hold such drug, and a user control structure at the accessing device's proximal end. The tool further includes a tissue-penetrating implement carried at the accessing device's distal end for axial movement into and out of the lumen. The implement has first and second expandable members which are disposed in a substantially co-extension condition, when the implement is disposed in a retracted condition within the lumen. Alternatively, the implement may assume an expanded, spaced-apart condition when the implement is advanced to an extended condition out of the lumen. At least one of the members has a tip for penetrating such tissue. A first operative connection exists between the control structure and the implement that is operable, upon user activation of the control structure, to advance the implement from its retracted to its extended condition. When the accessing device's distal end is placed against a surface region of the tissue, the implement is advanced into the tissue, causing the two expandable members to expand to form a cavity within the tissue. A second operative connection exists between the control structure and the reservoir that is operable, upon user activation of the control structure,—to deliver drug from the reservoir into such cavity. Placement of the accessing device's distal end against a surface region of such tissue, and activation of the control structure results in the delivery of drug into a cavity within the tissue.

In another embodiment, the implement includes at least two expandable elements which move away from one another as the implement is being advanced, from its retracted to its extended condition, into such tissue, to form a cavity in the tissue.

In yet another embodiment, the second expandable member of the tissue penetrating implement defines a lumen having a plurality of openings that permit direct communication of an drug passed into a cavity formed by the tool with at least about 90% of the surface area of the tissue directly bordering the drug receiving space.

In a particularly preferred embodiment, the accessing device is a flexible catheter accessing device; and further comprises a pull-wire assembly extending longitudinally through the catheter accessing device, the pull-wire assembly being operable to deflect the distal end of the accessing device substantially within a plane; and one or more force contact transducers mounted at the distal end of the accessing device within the deflection plane. This embodiment may further comprise one or more additional force contact transducers mounted at the distal end of the accessing device outside of the deflection plane.

In another embodiment, the first expandable member further comprises construction from a shape memory material capable of a first remembered curved shape, and a second, stress induced linear shape causing the first expandable member to cut in an arc shape as it is advanced through a tissue upon extension from the confines of the accessing device lumen.

In still another embodiment, the second expandable member comprises a ribbed balloon, wherein each rib defines a lumen in fluid communication with the drug-delivery reservoir, and each rib further defines a plurality of exit ports from the rib lumen that the drug may perfuse through into the formed cavity.

In another embodiment, the first expandable member is formed in a corkscrew shape tubular member defining a lumen within exiting at an end distal to the accessing device and in communication with the drug-delivery reservoir, the first expandable member is rotatable along its axis to permit it to screw into a tissue upon axial rotation, and, upon stopping axial rotation, withdraw into the lumen of the accessing device thereby pulling the tissue up into the lumen of the accessing device until such tissue is sealably urged against the accessing implement's lumen edge causing a seal to form between the accessing implement's lumen edge and the tissue, and further causing a cavity to form between the distal region of the first expandable member and the tissue adjacent to that region.

In one embodiment, some of the expandable members of the tissue-penetrating implement define lumens with a plurality of openings in fluid communication with the drug-delivery reservoir such that a drug may be introduced into a formed cavity with at least about 90%, and preferably greater than about 95%, of the surface area of the tissue directly bordering the cavity.

The accessing device can be, for example, a flexible catheter accessing device or the accessing device of an endoscope-type tool. In an embodiment of the former (i.e., a catheter-type tool), the tool further includes (i) a pull-wire assembly extending longitudinally through the catheter accessing device, with the pull-wire assembly being operable to deflect a distal-end region of the accessing device substantially within a plane; and (ii) one or more (for example, two) ultrasound or force contact transducers mounted on opposing sides of the orifice at the distal end of the accessing device within the deflection plane. Optionally, one or more (for example, two) additional transducers can be mounted at the distal end of the accessing device outside of the deflection plane.

One aspect of the present invention provides an drug-delivery tool for delivering a selected diagnostic or therapeutic agent to a target site within a selected body tissue, such as myocardial tissue of the heart. Generally, the drug delivery tool includes an accessing device having proximal and distal ends, with a lumen extending between such ends and terminating at an orifice at the distal end. A tissue-penetrating implement is movable between a retracted condition, within a distal region of the lumen, and an extended condition, extending out of the orifice. The tissue-penetrating implement includes a tip configured to penetrate a selected body tissue when (i) the distal end of the accessing device is placed there against and (ii) the implement is advanced from its retracted condition to its extended condition. In addition, the tissue-penetrating implement includes a first expandable member, disposed proximal of the tip, for following the tip to a target site as the tip penetrates the selected tissue. A second expandable member, also proximal to the tip of the implement, is adapted to expand radially as the implement is advanced to its extended condition, with a force sufficient to form a cavity at the target site by pressing the tissue adjacent the penetration site away from the longitudinal axis of the implement. An agent-delivery passage or conduit extends longitudinally through at least a member of the accessing device, with a distal end of the passage defining an exit port facing the expandable member of the tissue penetrating implement. By this construction, an agent, passed or drawn through the passage and out of the exit port, is directed into a central region of the expandable member, and any cavity formed thereby.

In one embodiment, the tissue-penetrating implement of the drug-delivery tool includes (i) a cutting or slicing tip at its distal-end region, and (ii) one or more resiliently flexible expandable members extending proximally therefrom, with the expandable members being adapted to expand radially outward in their normal state. The expandable members can be, for example, wires or filaments made of Nintinol, or the like. Movement of the tissue-penetrating implement can be effected using an actuation line attached at one end to a proximal end of the implement and attached at its other end to a manually operable deflection mechanism at a proximal end of the drug-delivery tool. By this construction, sliding movement of the line within the accessing device is transmitted to the implement—causing the implement to move.

The agent-delivery passage of the drug-delivery tool can be formed, for example, by an elongate conduit having an internal lumen that extends between the proximal end of the accessing device and a distal-end region of the accessing device. In one embodiment, such a conduit is adapted for sliding movement within the accessing device, coupled with movement of the tissue-penetrating implement.

One embodiment of the drug-delivery tool, particularly useful for delivering a selected agent having a net negative charge (for example, DNA), further comprises first and second electrodes adapted to be placed in electrical communication with a power supply. The first electrode, in this embodiment, is disposed at a distal region of the tissue-penetrating implement and the second electrode is disposed proximally of the implement. Generation of a positive charge at the first terminal is effective to draw at least a portion of the negatively charge species from a supply or holding reservoir, through the agent-delivery passage, and into the expandable member of the tissue-penetrating implement.

Another embodiment of the-drug-delivery tool is particularly well suited for placing a solid or semi-solid agent in a cavity formed by the cavity forming implement, and then permitting the agent to move outwardly as portions of it dissolve or otherwise slough off. In one particular construction, the expandable member of the tissue-penetrating implement includes a plurality of resiliently flexible expandable members (for example, wires or filaments of Nintinol, or the like) disposed at spaced positions about the longitudinal axis of the implement so as to define, a cage or skeleton capable of holding the agent as it is placed in a cavity formed by the implement. The cage is provided with open regions between its expandable members sufficient to provide direct exposure of the agent to at least about 95% of the tissue bordering the cavity.

Another general embodiment of the drug-delivery tool of the invention includes (i) an accessing device having proximal and distal ends, with a lumen extending there between and terminating at an orifice at the distal end; (ii) a tissue penetrating implement movable between a retracted condition, within a distal region of the lumen, and an extended condition, extending out of the orifice; with the implement including (a) a tip configured to penetrate a selected body tissue when the distal end of the accessing device is placed there against and the implement is moved from its retracted condition to its extended condition, and (b) a cage member disposed proximal of the tip for following the tip to a target site within such tissue, and adapted to assist in the formation and maintenance of a cavity at the target site by pressing the tissue at the target site away from the longitudinal axis of the implement as it is inserted therein and having sufficient rigidity to resist inwardly directed forces of the tissue tending to collapse the cavity; and (iii) an agent-delivery passage extending longitudinally through at least a member of the accessing device, with a distal end of the passage defining an exit port facing the cage member for directing a selected agent, passed through the passage, into a central region of the cage member and any such cavity formed thereby.

The cage member can comprise, for example, a plurality of expandable elements disposed about the central, longitudinal axis of the implement, with open regions between adjacent expandable members. Preferably, at least about 95% of the cage member is open. The cage member can be expandable (tending to flex outwardly), or generally non-expandable.

In another of its aspects, the present invention provides a method for delivering a selected diagnostic-or therapeutic agent, to-a target site within a selected body tissue.

According to one general embodiment, the method includes the steps of:

(i) forming a cut or slice extending from a wall of the selected tissue to the target site;

(ii) moving or pressing the tissue bordering the cut or slice radially outward, thereby forming a cavity within the tissue at the target site;

(iii) delivering a selected agent into the cavity, with the cavity being maintained; and (iv) permitting the cavity to collapse once a selected amount of the agent has been delivered therein.

In one embodiment, at least about 90% (and preferably greater than 95%) of the surface area of the tissue bordering the cavity is directly exposed to the cavity, so that the agent delivered into the cavity can pass directly into the exposed tissue.

Step (i) of the method (i.e., cutting/slicing) is preferably effected using a cutting or slicing implement, such as a blade edge or tip, that is configured to avoid the removal of tissue along the region of the cut or slice beyond the inherent cellular injury due to the cutting or slicing.

According to one embodiment, the cut or slice formed in step (i) is made along a substantially linear axis, with the axis being oriented generally normal to the wall of the selected tissue. Ultrasound can be used to achieve such orientation.

The agent can be delivered using, for example, an elongate agent-delivery conduit defining a passage or lumen terminating at a distal orifice through which the agent can exit Preferably, during delivery of the agent using such a tool, the orifice does not make substantial contact with the selected tissue, thereby maximizing the tissue surface area available for contact with the agent.

In one embodiment, the selected tissue is heart tissue (for example, myocardial tissue), and the cut or slice is formed from an endocardial wall, a septal wall, or an epicardial wall.

In another embodiment, the selected tissue is stunned, ischemic and/or hibernating organ tissue that has at least partially lost its normal capillary ability at vasomotion. The greater surface area and capillary access provided by practicing the present invention permits the agent to be moved through micro-capillaries even where assistance by natural vasomotion is greatly diminished or unavailable.

A wide variety of agents can be delivered using the present invention. The selected agent can be, for example, an angiogenic agent (for example, a protein and/or nucleic acid). In one embodiment, the agent is a nucleic acid, for example, naked DNA, intended for delivery to heart tissue.

A further aspect of the present invention provides a method where the normal pressure drug tissue treatment area of 5–10 mm obtained with direct needle injection or TMR can be improved upon by creating a temporary cavity having significantly greater direct capillary access due to surface area, lack of nonperfusing delivery implement to cell contact patches and implement stretching force.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which.

DETAILED DESCRIPTION OF THE INVENTION

The following discussion of the preferred embodiments of the present invention is merely exemplary in nature. Accordingly, this discussion is in no way intended to limit the scope of the invention.

Figure 3:
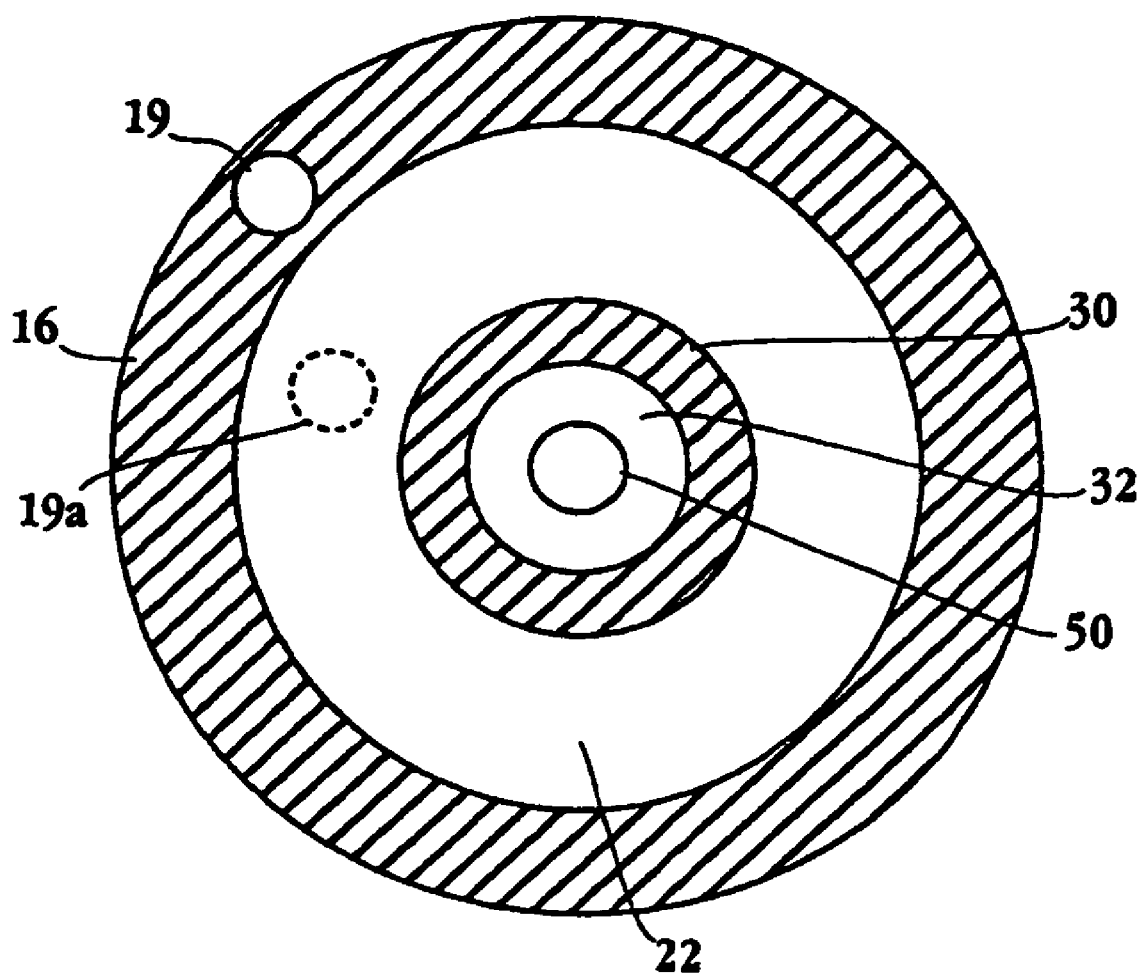
FIG. 3 is a cross sectional view of the catheter assembly shown in FIG. 1, taken laterally across a mid-member of the catheter accessing device.

An exemplary drug-delivery tool which embodies various features of the invention is shown in FIGS. 1 through 4. As will become apparent, the illustrated drug-delivery tool is particularly well suited for percutaneous introduction into a subject for intravascular delivery of a selected agent into temporary cavities formed in a desired layer of a selected tissue. With initial reference to FIG. 1, a catheter assembly (which may be disposable, in whole or in part), indicated generally by the reference numeral 12, includes a control structure (hand unit) 14 attached to a steerable catheter accessing device 16 having a controllably deflectable distal-end member. Steering of the catheter assembly can be accomplished in a variety of ways. For example, the catheter assembly can include steering components like those disclosed in U.S. Pat. No. 5,876,373, entitled "Steerable Catheter," to Giba et al.; and/or in co-pending U.S. Provisional Patent Application Ser. No. 09/080,175 filed May 16, 1998, entitled, "Drug Delivery Module," to Glines et al.; and/or in published European Patent Application No. EP 0 908 194 A2, each of which is expressly incorporated herein by reference. Briefly, in the illustrated embodiment, a pull wire 18, having an enlarged head member 18*a* at its distal end, extends from the tip of catheter accessing device 16, through a wire-guide channel 19 extending through catheter accessing device 16, to control structure (hand unit) 14, whereat the wire's proximal end is coupled to a deflection or steering actuator assembly. Rotation of a deflection knob 20, which is threadedly mounted along a forward end of the hand unit, causes the pull wire to be pulled backward, or the catheter accessing device to be pushed forward, relative to one another, thereby inducing deflection of the distal end of the steerable catheter accessing device. Rather than running the pull wire through a channel extending through the catheter accessing device, another embodiment provides the pull wire extending longitudinally along the interior wall of the catheter accessing device (FIG. 3). Other steering mechanisms and arrangements, suitable for use herein, will be apparent to those skilled in the art. In yet another preferred embodiment, the catheter is further guided by a coaxial second catheter as described in co-pending application U.S. Ser. No. 09/052,971 and PCT publication WO 9949773A2 titled "Delivery catheter system for heart chamber" by Payne, filed Mar. 31, 1998, both herein incorporated in their entireties by reference.

Catheter accessing device 16 is dimensioned to be placed in the vasculature of a subject and steered therethrough until the tip is disposed adjacent a selected region of tissue, for example, a surface or wall within a heart chamber (such as against the endocardial wall within the heart's left ventricle).

Visualization enhancement aids, including but not limited to radiopaque markers, tantalum and/or platinum bands, foils, and/or strips can be placed on the various components of drug-delivery tool—catheter assembly 12, including on the deflectable end member of catheter accessing device 16. In one embodiment, for example, a radio-opaque marker (not shown) made of platinum or other suitable radio-opaque material is disposed adjacent the tip for visualization via fluoroscopy or other methods. In addition, or as an alternative, one or more ultra-sonic transducers can be mounted on the catheter accessing device at or near its tip to assist in determining its location and/or placement (for example, degree of perpendicularity) with respect to a selected tissue in a subject, as well as to sense wall contact with, and/or wall thickness of, the tissue. Ultra-sonic transducer assemblies, and methods of using the same, are disclosed, for example, in published Canadian Patent Application No. 2,236,958, entitled, "Ultrasound Tool for Axial Ranging," to Zanelli et al., and in co-pending U.S. patent application Ser. No. 08/852,977, filed May 7, 1997, entitled, "Ultrasound Tool for Axial Ranging," to Zanelli et al., each of which is expressly incorporated herein by reference. In one embodiment of the present invention, depicted in FIG. 2, two transducers, denoted as 26 and 28, are angle mounted at the tip of catheter accessing device 16 in the axis of pull-wire deflection. This construction permits an operator to determine, by comparing signal strength, whether the catheter tip region is perpendicular to a selected tissue surface or wall. Additionally, this two transducer arrangement provides the operator with information useful for determining an appropriate adjustment direction for improving perpendicularity, as compared to single-transducer arrangements that, while capable of indicating perpendicularity by signal strength amplitude, are generally incapable of indicating a suitable direction in which to move the tip to improve perpendicularity. In a related embodiment, third and fourth transducers (not shown) are added, off of the deflection axis, to aid an operator with rotational movement and rotational perpendicularity in the non-deflecting plane of the subject tissue surface. Each of the above ultrasound transducers may preferably be substituted with force contact transducers described in co-pending U.S. Provisional patent application No. 60/191,610 by C. Tom titled "Apparatus and method for affecting a body tissue at its surface", filed Mar. 23, 2000, herein incorporated by reference. An additional benefit of using a force contact transducer is that the contact force and incident angle are know to the user enabling the user to achieve a seal between the distal end of the accessing device and a tissue such that a seal is formed between the two preventing administered drug from seeping out of a formed cavity.

Figure 1:
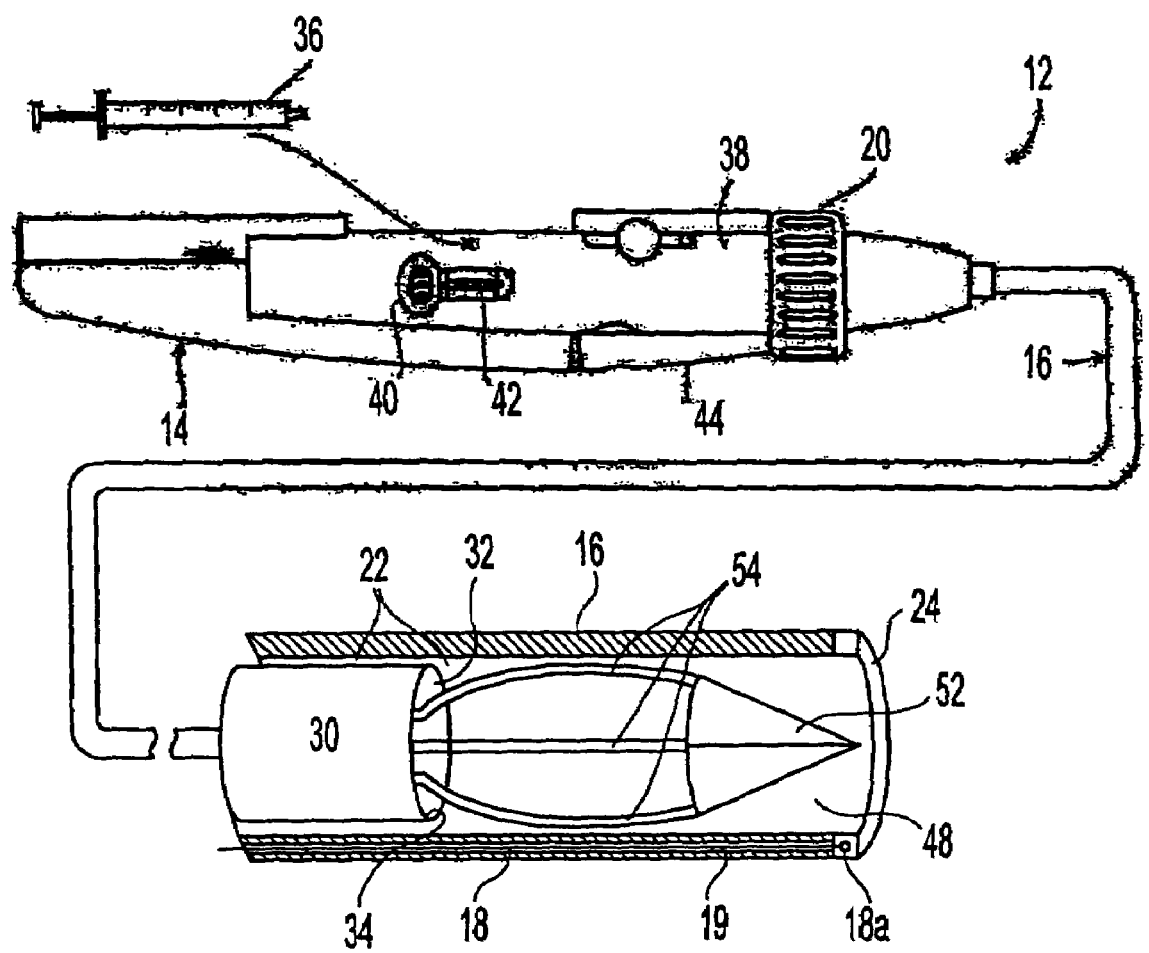
FIG. 1 is an elevational view of a steerable catheter assembly, with its distal end region enlarged and in section showing a tissuepenetrating implement therein, as taught by an embodiment of the present invention.
Figure 2:
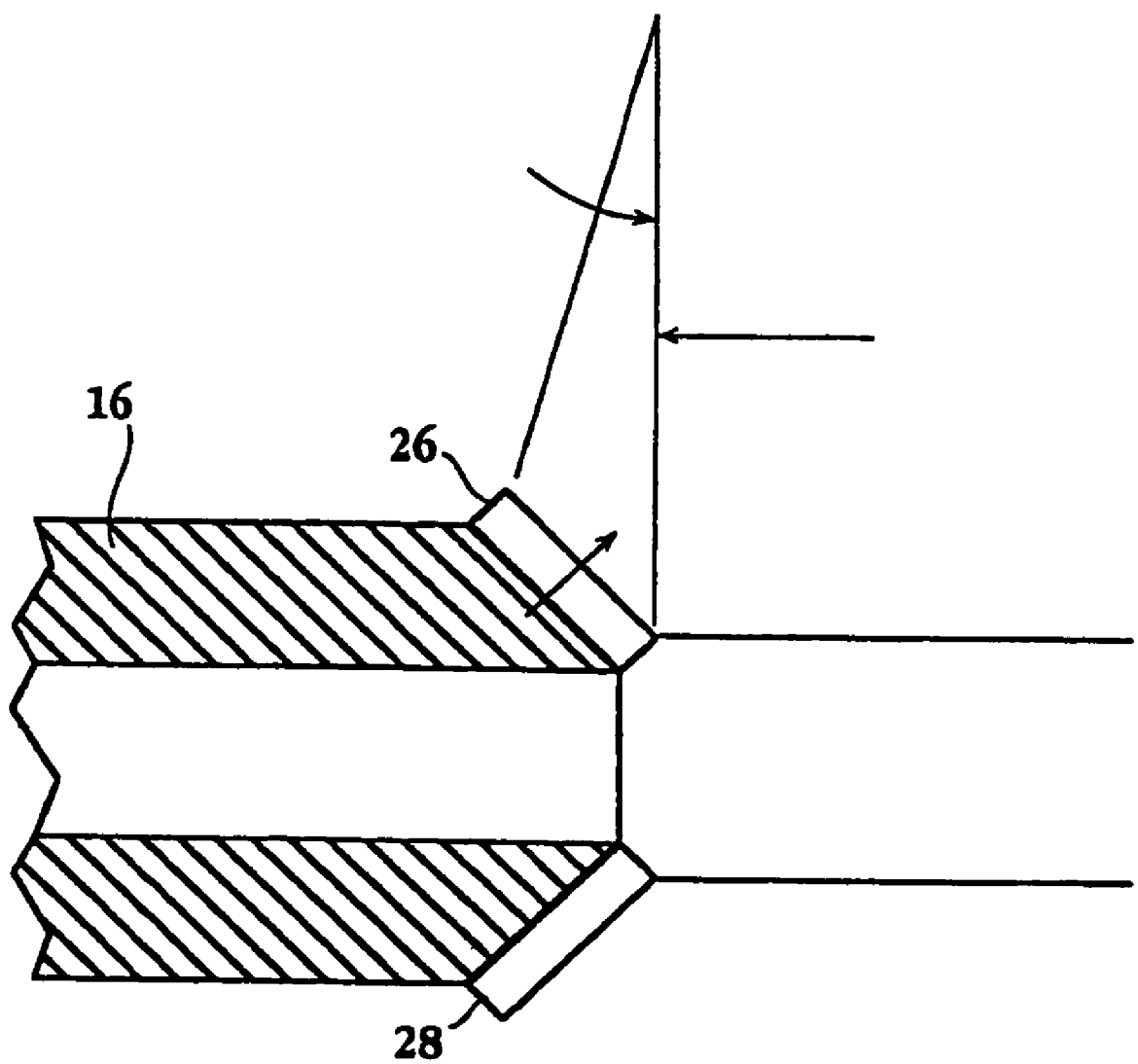
FIG. 2 is a side sectional view showing two angle-mounted ultrasound transducers on the distal end of a steerable catheter accessing device, in accordance with an embodiment of the present invention.

In some preferred embodiments, one or more elongate lumens may extend between the proximal and distal ends of the catheter accessing device, with (i) at least one lumen being dimensioned to accommodate a cavity forming implement for axial movement along a region of the assembly's distal end, and (ii) at least one lumen being configured to permit passage of one or more selected therapeutic and/or diagnostic agents from an agent-supply region (for example, a reservoir in the hand unit) to, and out of, a terminal orifice at the assembly's distal end. The just-described items (i) and (ii) can be achieved using a single lumen, or multiple lumens. In one embodiment, for example, catheter accessing device 16, as depicted in FIG. 1, is preferably formed with an outer diameter of between about 2.25 to 2.75 mm (preferably 7 French), and an inner diameter, defining a primary lumen 22, of about 1 mm. At its distal end, lumen 22 terminates at an orifice 24. A tissue-penetrating implement 48 (described below) is adapted for movement within a distal-end region of lumen 22. A selected agent can be passed through the main lumen directly, i.e., in contact with the main lumen's interior walls, and/or indirectly, for example, using one or more additional lumens (for example, sub-lumens) extending coextensively and/or coaxially with the main lumen. An embodiment of the latter construction is also illustrated, in part, in FIGS. 3 and 4. For example, FIGS. 1, 3, and 4 each depict different aspects of an elongate, flexible agent delivery conduit 30 is disposed substantially coaxially within catheter accessing device 16, extending from control structure (hand unit) 14 to a distal region of lumen 22. Conduit 30 can be formed, for example, of a substantially inert polymeric material that resists collapse during bending or twisting, such as braided polyimide, braided PEBAX, or the like. Conduit 30 defines a hollow, axial lumen or passage 32, having a diameter within a range of from about 0.25 mm to about 1 mm (for example, about 0.5 mm), or from about 0.010" to about 0.040" (for example, about 0.020"), that communicates at its proximal end with an agent supply reservoir disposed in control structure (hand unit) 14, and terminates at its distal end at an exit or infusion port 34, through which a selected therapeutic and/or diagnostic agent can pass. As described below, conduit 30 is adapted for reciprocal sliding movement within catheter accessing device 16 and, thus, is provided with an outer diameter less than the inner diameter of catheter accessing device 16, for example, about 1 mm or less in certain constructions.

At this point, certain details of the hand unit relating to agent storage and dispensing will be described, bearing in mind that additional details are set forth in co-pending U.S. Provisional Patent Application Ser. No. 09/080,175 filed May 16, 1998, entitled, "Drug Delivery Module," to Glines et al., incorporated herein by reference. In one preferred embodiment depicted in FIG. 1, control structure (hand unit) 14 is provided with a fixed drug-delivery reservoir for holding a supply of a selected agent to be dispensed. In this embodiment, a supply vessel, such as syringe 36, can communicate with the drug-delivery reservoir via a connector provided in the unit's outer housing 38. The connector is preferably a substantially sterile connector, such as a standard Luer-type fitting or other known standard or proprietary connector. In another embodiment, the supply reservoir comprises a syringe, pre-loaded with a selected agent, that can be removably fit into a holding area inside the housing. In both such embodiments, a dosage volume adjustment thumbscrew 40 can be mounted in the housing 38 so as to be externally accessible for accurate, local and rapid dosage volume adjustment. Also, a dosage volume scale or indicator, as at 42, can be provided in the housing 38. Upon depressing a trigger mechanism 44 along one side of control structure (hand unit) 14, manually or otherwise, the agent stored in the drug-delivery reservoir moves into conduit 30. It should also be noted that trigger mechanism 44 is coupled to the proximal end of conduit 30 such that, upon being depressed, the conduit is pushed forward (advanced) within catheter accessing device 16 from a normal, retracted condition, depicted in FIG. 1, to a dispensing condition, shown in FIG. 4, whereat conduit orifice 34 can be positioned closely adjacent a selected tissue, such as 46, against which catheter-accessing device orifice 24 has been placed. Upon releasing the trigger mechanism, conduit 30 shifts back to its normal condition. The distance traversed by conduit 30, in each direction, is from about 2 to about 10 mm, and preferably about 5 mm.

A tissue-penetrating implement, indicated generally as 48, is also longitudinally movable within catheter accessing device 16, between a retracted condition, within a distal region of lumen 22 (FIG. 1), and an extended (advanced) condition, passed through and extending out of orifice 24 (FIG. 4), over a stroke of about 4–6 mm, and preferably about 5 mm. Movement of implement 48 is effected by way of an elongate actuation line 50, depicted in cross-section in FIG. 3, operatively coupled at one end to trigger mechanism 44 (FIG. 1) and extending axially through conduit 30 from control structure (hand unit) 14 to a proximal end of implement 48. Preferred materials for forming the actuation line are laterally flexible, permitting movement through tortuous pathways, and sufficiently incompressible along the longitudinal direction to provide for the efficient transmission of motion from the proximal end to the distal end. Suitable materials include, for example, stainless steel or a braided composite. In operation, upon the depressing trigger mechanism, implement 48 is shifted from its normal, retracted condition, to its extended condition, and upon release of the trigger mechanism, implement 48 returns to its retracted condition.

For reasons that will become apparent below, it should be noted that the above-described advancement of both conduit 30 and cutting implement 48 takes place substantially simultaneously (i.e., these motions are coupled) with a single depression of trigger mechanism 44. In addition, optionally, with the same trigger depression, an agent held in a reservoir in the hand unit is dispensed from conduit 30. Preferably, such dispensing is effected immediately after (not before) the conduit and cutting implement have reached their respective extended conditions. For example, the initial depression can actuate axial movement of the conduit and cutting implement, and the latter member of the depression can effect dispensing. Similarly, both conduit 30 and cutting implement 48 are retracted together with release of the trigger mechanism, and the dispensing of the selected agent is stopped.

With further regard to the tissue-penetrating implement 48, its distal end includes a cutting or slicing tip, denoted as 52. In the illustrated arrangement, tip 52 takes the form of a narrow, three-sided pyramid-like structure that tapers to a sharp point. Alternatively, tip 52 could taper to a two-sided knife edge or blade, or any other suitable cutting or slicing structure. Preferred cutting or slicing structures are configured to substantially avoid the removal of tissue beyond the cellular injury inherent in cutting.

Figure 4:
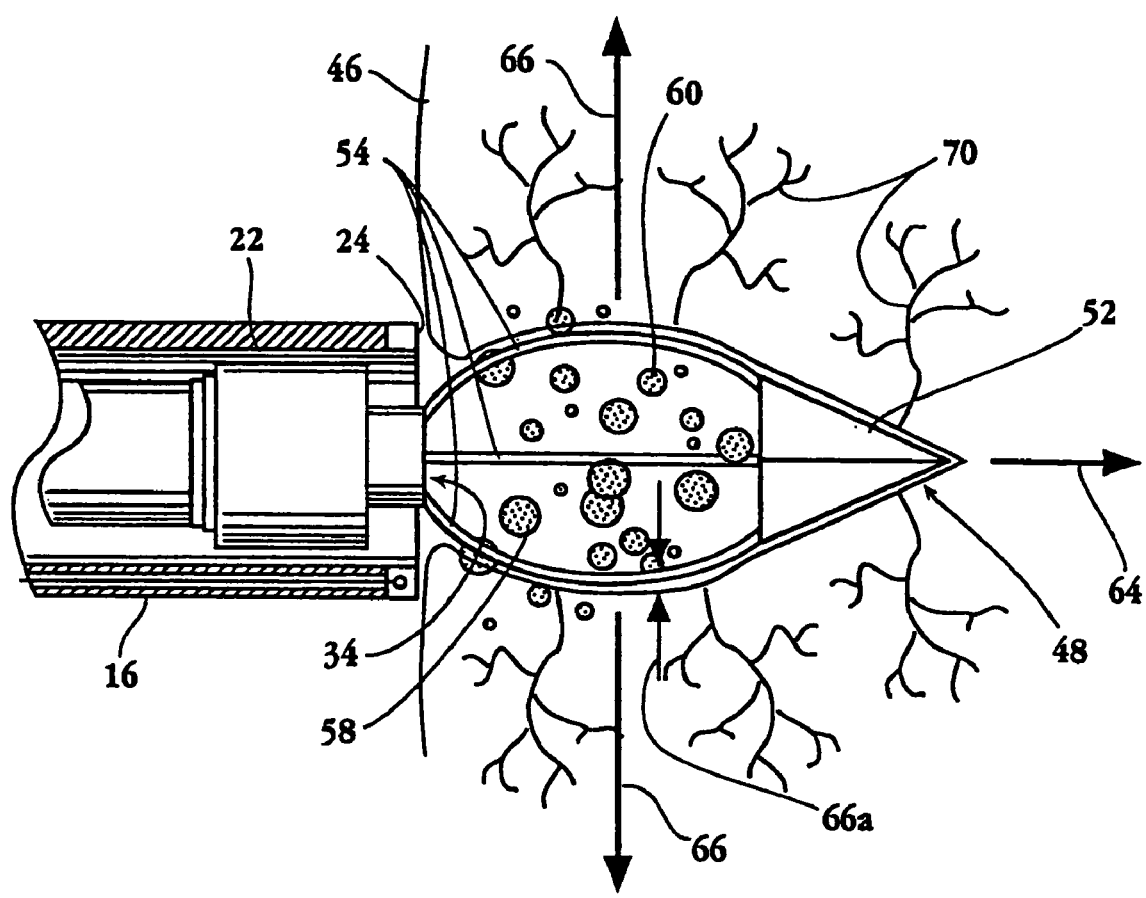
FIG. 4 is a side sectional view of the catheter-assembly distal-end region of FIG. 1, taken longitudinally therealong, with the tissuepenetrating implement inserted into a selected tissue to form a cavity therein for receiving a selected agent.

Implement 48 further includes an expandable member, proximal of tip 52, comprised of one or more resiliently flexible expandable elements or expandable members, three of which are visible (out of a total of four) at 54 in the embodiment of FIGS. 1 and 4. The expandable members are arranged at spaced positions about the implement's longitudinal axis, and configured to flex outwardly, away from such axis, to collectively form a three dimensional support skeleton or cage. The expandable members can be, for example, narrow, elongate wires, filaments or ribbons, formed of a substantially inert, resiliently flexible material, such as a metal or metal alloy (for example, stainless steel, nickel-titanium, or similar material) or from an injection molded plastic. The distal end of each expander is turned inward and attached to the proximal side of tip 52. When the expandable member is disposed at its retracted condition (FIG. 1), the expandable members are compressed toward the implement's longitudinal axis; and when advanced to its extended condition (FIG. 4), the expandable members are allowed to flex outward, so that, overall, the expandable member achieves a maximum diameter of about 1–3 mm, and preferably from about 1.75 mm to about 2 mm.

According to one preferred construction of the expandable member, between about 3–10 nickel-titanium (for example, as available commercially under the name "Nintinol") filaments, each between about 4–5 mm in length and from about 0.003" to about 0.005" in diameter are employed as expandable members. The particular number, dimensions, and material composition of the expandable members are not critical, provided only that the expandable members are capable of forming a cavity when inserted into a selected tissue (i.e., they have sufficient strength and spring capabilities), and, when in the expanded condition, a drug or other agent delivered into the region within the expandable members can move outwardly into the tissue about the cavity, with very little interference presented by the expandable members themselves, as shown in FIG. 4 with agent 58 in cavity 60. Regarding the latter, the expandable members preferably occupy no more than about 10%, and more preferably less than about 3%, of the region defining the boundary between the cavity and the target tissue thereabout. In this way, the vast majority of the tissue boarding a cavity can be directly exposed to an agent delivered into the cavity.

An exemplary method of using the above catheter assembly will now be described, wherein the catheter assembly is used for intra-myocardial delivery of a selected therapeutic and/or diagnostic agent. Initially, catheter accessing device 16 is percutaneously introduced via femoral or radial artery access. This can be accomplished, for example, by way of the Seldinger technique (*Acta Radiologica*, 38, [1953], 368–376; incorporated herein by reference), a variation thereof, or other conventional) technique. Optionally, a conventional guiding or shielding catheter (not shown) can be employed to assist in tracking the catheter tool through the patient's vasculature and into targeted regions of the heart. Once arterial access is established, the catheter accessing device 16 is slid across the aortic valve and into the left ventricle chamber. The distal end of the catheter accessing device 16 is maneuvered so as to be substantially perpendicular to the endocardial wall 46 (FIG. 4), using fluoroscopic visualization and/or ultrasound guidance, and pressed thereagainst. Trigger mechanism 44 is next depressed, causing cutting tip 52 to advance into the myocardial tissue, in the direction of arrow 64, to a preset or adjustable depth. Expandable members 54 follow cutting tip 52 into the myocardium and expand radially (for example, in the direction of arrows 66), creating a cavity about the axis of penetration (i.e., the axis of cutting or slicing). Once the cavity has been created, the expandable members serve to maintain the cavity by resisting heart contractile forces. The same trigger depression serves to deliver a selected agent through conduit 30 into the cavity 60. After allowing the agent to enter into the surrounding tissue for appropriate period of time, for example, typically less than about 2 minutes, the tissue-penetrating implement is withdrawn, at which point the cavity can close.

Figure 5A:
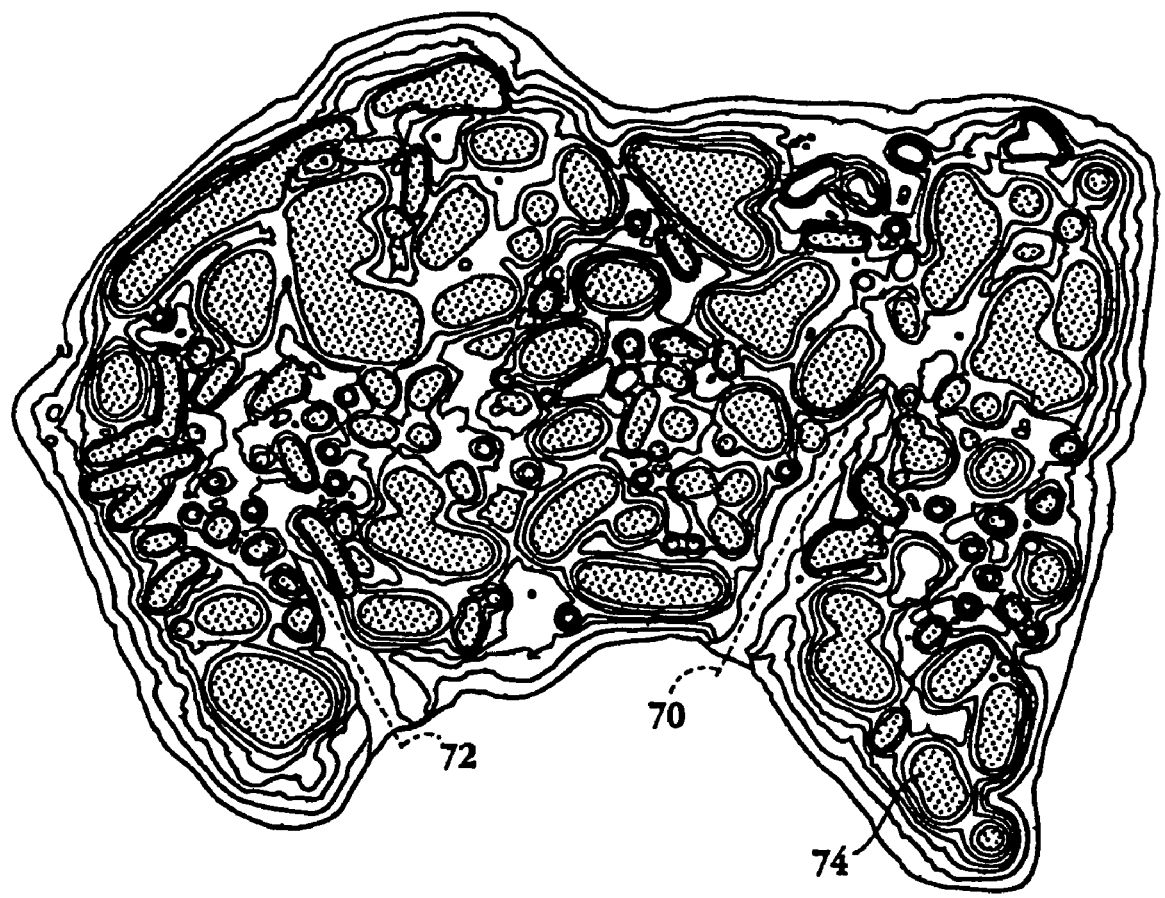
FIG. 5A illustrates a section of normal myocardial tissue.
Figure 5B:
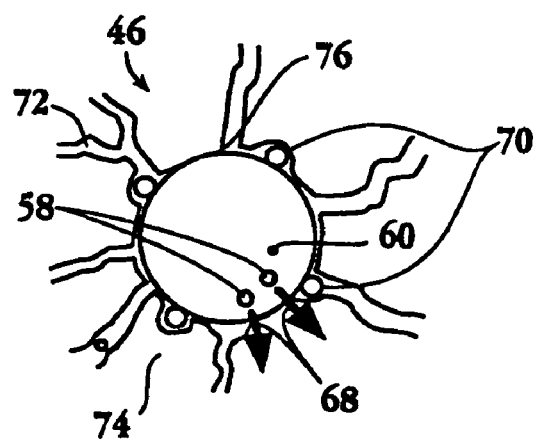
FIG. 5B illustrates a section of myocardial tissue with a temporary cavity formed therein.

Healthy myocardial tissue is illustrated in FIG. 5A. As shown, healthy tissue contains capillaries 70, interstitial tissue 72, and heart muscle cells 74 (See, for example, "Gray's Anatomy" (1959) at page 597). FIG. 5B shows how a temporary cavity 60 can be created to directly access, for example, along the direction of arrows 68, more capillaries 70, more heart muscle cells 74, and tissue surface area 76. It should be appreciated that the creation of temporary cavities, as taught therein, provides direct access to a greater number of capillaries than has been possible by the prior techniques. As a result, the performance of the infusate tool is greatly enhanced.

It is believed that abrasion to the wall of the cavities may aid in absorption of the agent. Accordingly, it may be desirable to configure the cutting tip and/or cavity expandable members of the invention so as to allow selective abrasion. This can also be accomplished, for example, by RF, thermal, acidic and/or ultrasonic means acting on the cutting tip and/or cavity expandable members.

It is noted that the above-described method is exemplary in nature. Those skilled in the art will appreciate that the present invention provides for the delivery of selected agents to a wide variety of body organs and regions.

Figure 6:
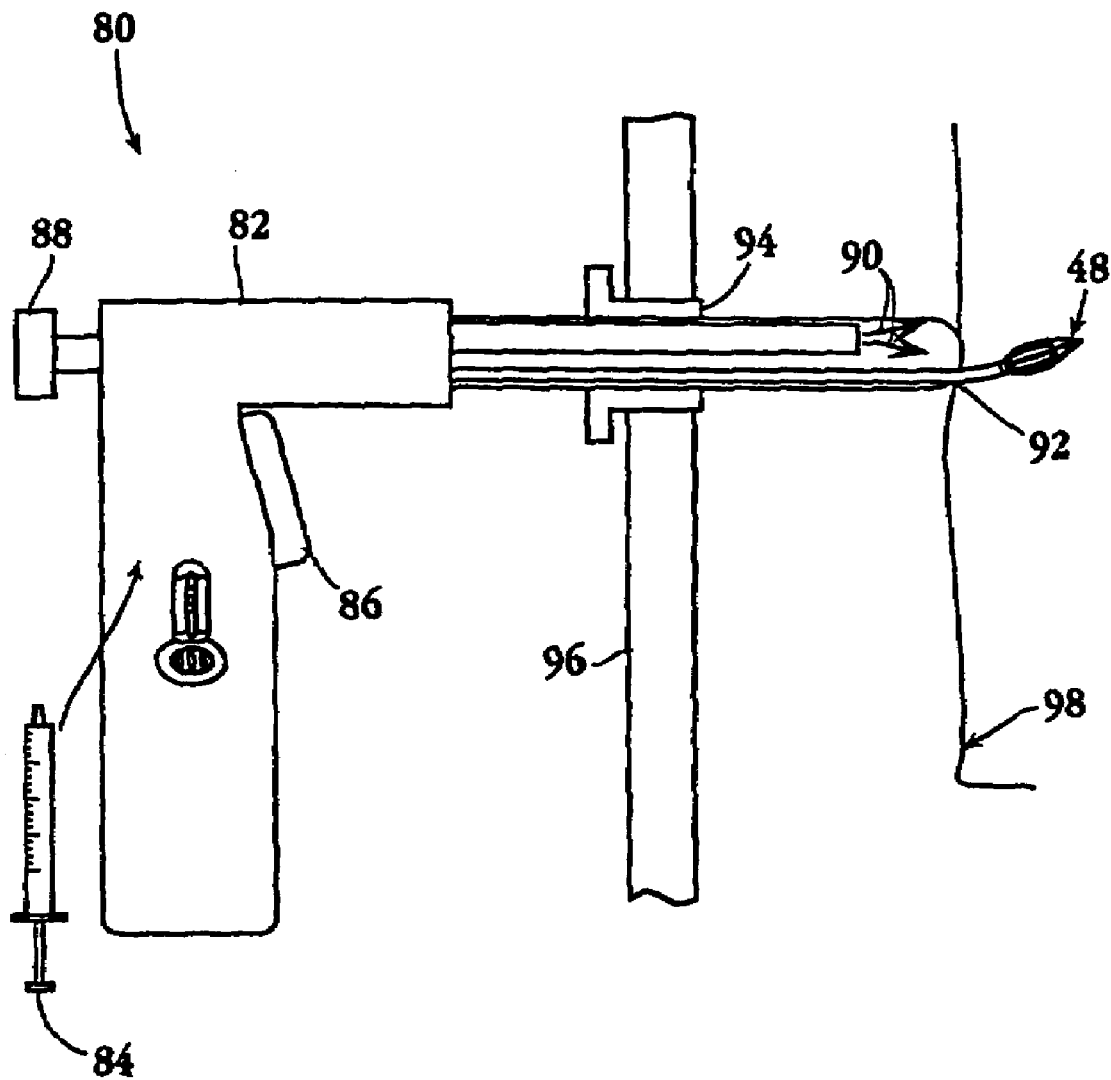
FIG. 6 is a side elevational view, with members shown in cross section, of an endoscope-type agent delivery tool having a tissuepenetrating implement like that of the catheter assembly of FIG. 1.

Another embodiment of the drug-delivery tool of the present invention is shown in FIG. 6, wherein the tool is embodied in an endoscope-type tool, shown generally at 80. As described next, the drug-delivery tool of this embodiment is configured for intraoperative use, to be introduced thoracoscopically or through a thoracotomy, to form temporary cavities in a selected tissue. The tool includes a proximal hand piece 82 (similar to the previously-described control structure (hand unit) 14) adapted to accommodate an drug-delivery reservoir syringe 84, and a depressible trigger mechanism 86. This particular surgical tool incorporates a reusable 5 mm thoracoscopic camera 88 axially mounted to provide an operator with a field of view 90 through lens 92. This allows the operator to work through a common Trocar access port 94 placed, for example, through a patient's chest wall 96. In an exemplary use, upon traversing the epicardial surface 98 of the heart, a tissue-penetrating implement 48, substantially as described above, can create a temporary cavity for receiving a selected agent. As with the catheter assembly, the tool is adapted to permit a user to both extend the tissue-penetrating implement and dispense a drug or other agent, with a single depression of the trigger mechanism 86. Additional details of the handpiece are presented in copending U.S. Provisional patent application Ser. No. 09/080,175 filed May 16, 1998, entitled, "Drug Delivery Module," to Glines et al., incorporated herein by reference. One skilled in the art would recognize that the above mentioned endoscopic embodiment may further be adapted for use without an endoscopic port, for example, such as in open surgery. Such an embodiment may be guided with or without visualization aids such as an optical endoscope or other optical enhancement device.

It should be noted that, especially when used in open surgery, the tissuepenetrating implement need not retract. Thus, movement of the implement between its retracted and advanced conditions, in such cases, need only involve movement of the implement move from its retracted to its advanced condition.

Figure 7A:
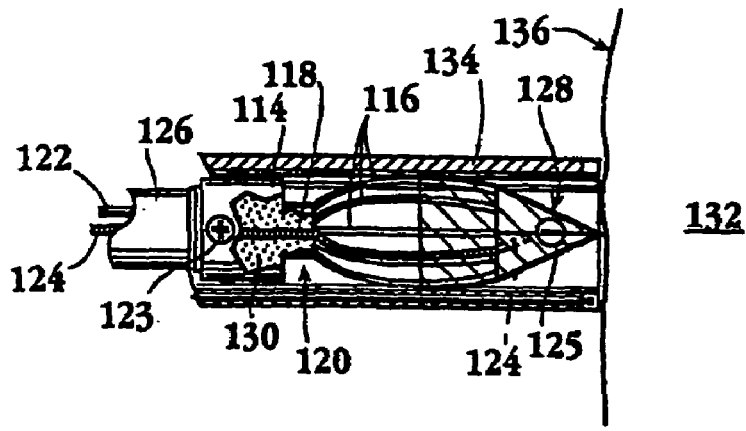
FIGS. 7(A)–7(C) illustrate an accessing device, shown in section, with a movable implement for forming a cavity in a selected tissue and delivering a selected agent therein, in accordance with the teachings of one embodiment of the present invention; and, FIGS. 8(A)–8(C) illustrate an accessing device, shown in section, with a movable implement for forming a cavity in a selected tissue and placing a selected agent therein, in accordance with an embodiment of the present invention.
Figure 7B:
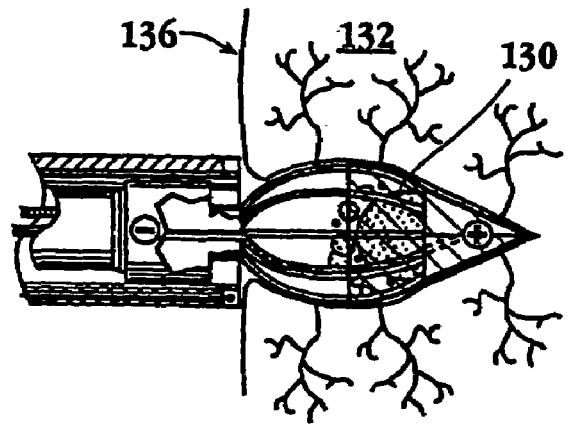
Figure 7C:
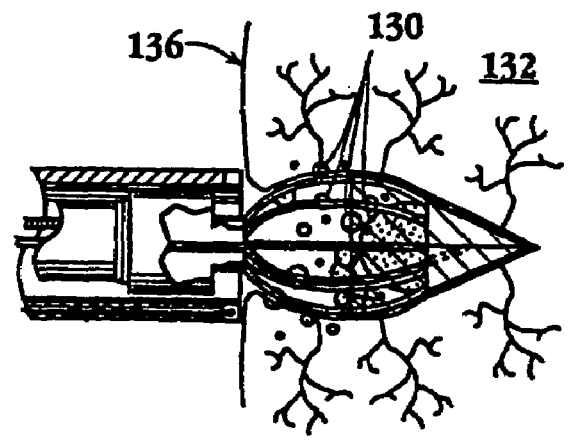

In another embodiment of the present invention, a selected therapeutic and/or diagnostic agent comprising a charged species (for example, DNA) is held within the distal-end region of an accessing device and delivered into a cavity formed by in a selected tissue via an electrical field. An exemplary cavity-forming and delivery implement, which can be incorporated in a catheter-type tool or an endoscope-type, such as previously described, is shown in FIGS. 7A–7C. Here, the implement includes drug-delivery reservoir or storage vessel 114 which opens into the region between a plurality of expandable members 116 via short passage 118 through a neck member 120. First and second lead wires, denoted as 122 and 124 respectively, extend through a flexible actuation accessing device 126 and terminate at respective terminals, or electrodes, fixed in the implement. The first terminal, indicated as 123, being placed at a rearward (proximal) region of the vessel 114, and the second terminal, denoted as 125, being placed at a forward (distal) region of the implement's cutting/slicing tip 128. In an exemplary operation, whereby DNA, indicated as 130, is delivered into myocardial tissue 132 of a subject, the catheter accessing device 134 is introduced into a subject body and placed against an endocardial or epicardial wall 136 of the heart's left ventricle (FIG. 7A). During such introduction and placement, the vessel terminal 123 is made positive (+) and the tip terminal 125 is made negative (−), thereby establishing an electrical field that maintains the negatively charged DNA in the vessel 114. It should be noted that the lead wires 122, 124 and regions about the terminals 123, 125 are shielded, using conventional materials, to limit the field's reach into the surrounding heart tissue. Such shielding about the forward (distal) region of the implement is indicated by back-hatching in the drawings. After placement of the catheter, actuation accessing device 126 is advanced, via a remote shifting mechanism (such as previously described), to push the slicing tip 128 through the wall 136 and into a region of myocardium 132, with the expandable members 116 following the tip therein. Once a cavity has been formed in the myocardium, the polarity is reversed, so that the tip terminal 128 is positive (+) and the vessel terminal 123 is negative (−) (FIG. 7B), thereby establishing an electrical field effective to draw the negatively charged DNA 130 toward the tip 128. After a short time, with at least a substantial member of the DNA drawn out of the vessel 114, the electrical field is discontinued (FIG. 7C), so that the DNA can move outwardly into the surrounding tissue and capillaries of the myocardium.

Figure 8A:
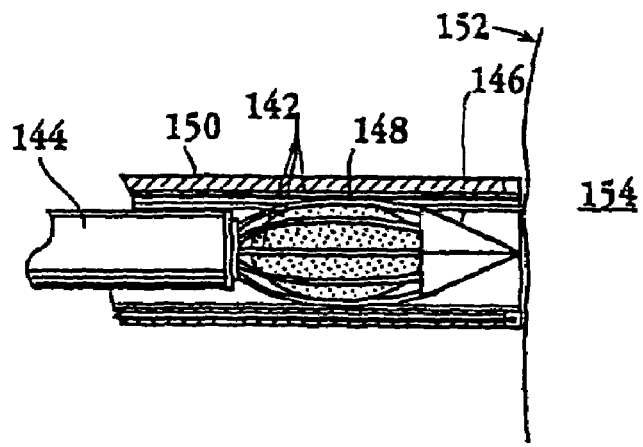
Figure 8B:
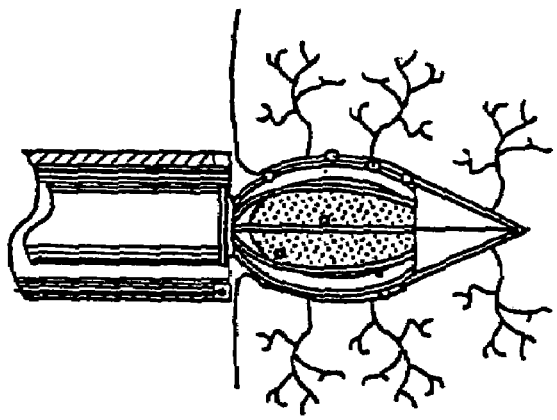
Figure 8C:
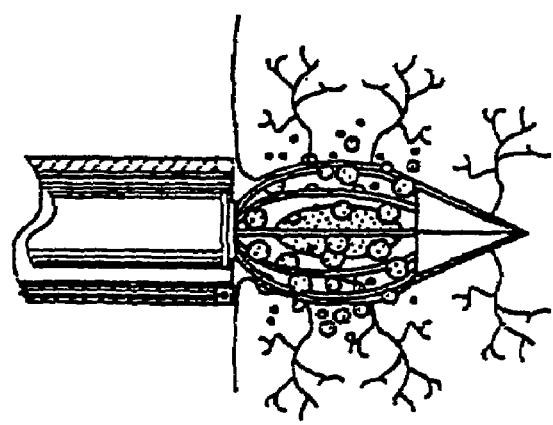

In another embodiment, a selected therapeutic and/or diagnostic agent is held within the distal-end region of an accessing device and placed in a cavity formed in a selected tissue. An exemplary cavity-forming and placement implement, which can be incorporated in a catheter-type tool or an endoscopetype, such as previously described, is shown in FIGS. 8A–8C. Here, the implement includes a plurality of expandable members 142 attached at their rearward (proximal) ends to a flexible actuation accessing device 144, and at their forward (distal) ends to a cutting/slicing tip 146. The expandable members 142 are arranged to serve as a cage or skeleton for containing a selected agent 148, in solid or semi-solid form, as the catheter accessing device 150 is placed against a selected organ wall, as at 152. (FIG. 8A). Actuation accessing device 144 is then advanced, via a remote shifting mechanism, to push the slicing tip 146 of the implement through the wall 152 and into a selected layer of tissue 154, with the expandable members 142 following the tip 146 therein (FIG. 8B). Once a cavity has been formed in this manner, the agent 148 is allowed to move outward into the surrounding tissue and capillaries (FIGS. 8B–8C). The agent can be configured to for controlled release after placement, for example, via swelling and sloughing over a period of several minutes. In one embodiment, wherein the agent is DNA, controlled-release preparations are formulated through the use of polymers to complex or absorb the selected gene sequence (with or without an associated carrier, for example, liposomes, etc.). The agents can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Nicolau, C. et al. (*Crit. Rev. Ther. Drug Carrier Syst.* 6:239–271 (1989)), which is incorporated herein by reference. In order to form a pharmaceutically acceptable composition suitable for effective administration, such compositions will contain an effective amount of the desired gene sequence together with a suitable amount of carrier vehicle.

Figure 9A:
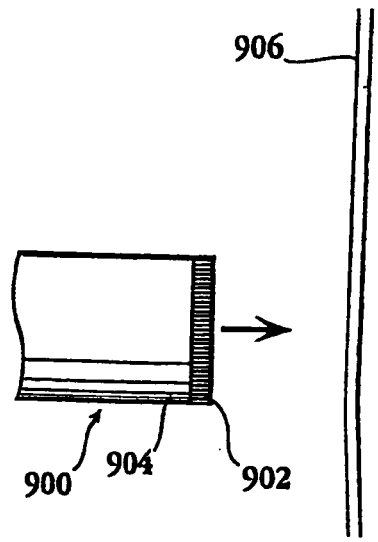
FIGS. 9 (a–d) depict an embodiment having a force contact transducer.
Figure 9B:
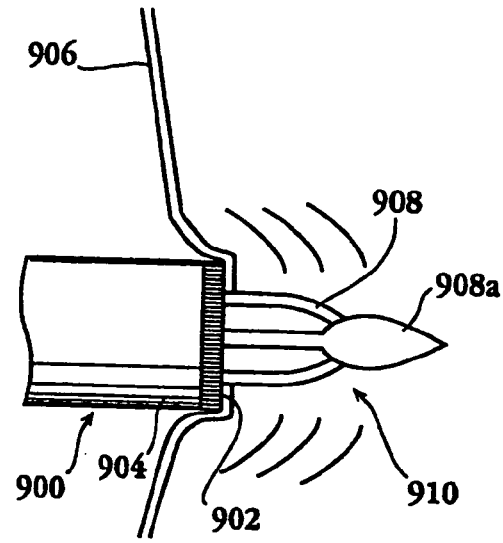
Figure 9C:
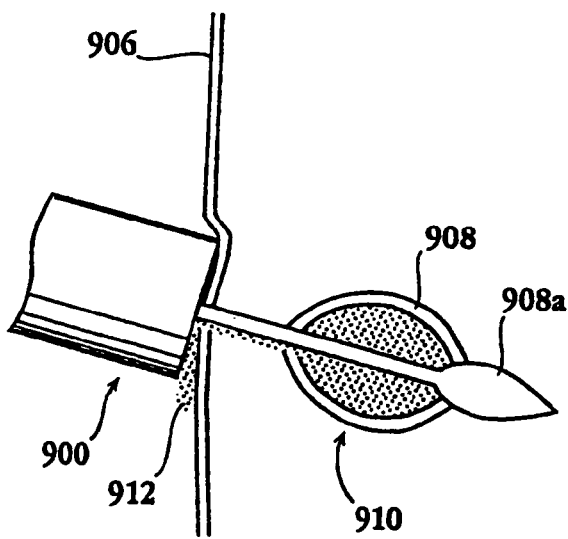
Figure 9D:
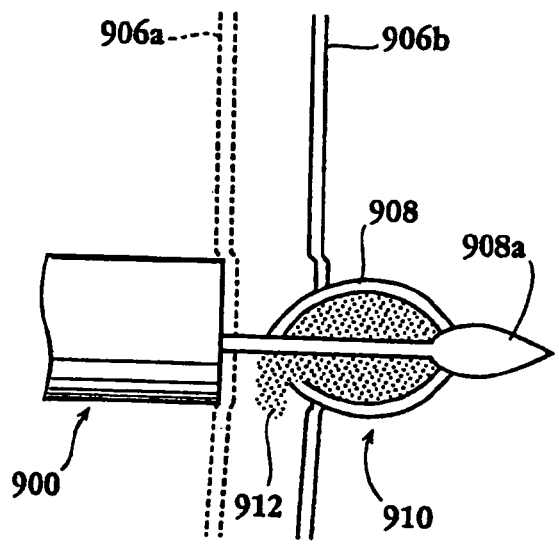

FIG. 9a depicts a preferred embodiment of the invention where accessing device 900 further comprises force contact transducer 902 mounted on distal end 904 of accessing device 900. As accessing device 900 is urged toward tissue 906, as shown in FIG. 9b, force contact transducer 902 contacts tissue 906 causing detectable contact pressure to develop between force contact transducer 902 and tissue 906. Such detectable pressure, detected by force contact transducer 902 is communicated back to the end user who then can further manipulate accessing device 900 to achieve perpendicularity between the thrust axis of accessing device 900 and tissue 906. Upon achieving perpendicularity and contact force, tissue-penetrating implement 908, with cutting tip 908a, may be advanced to an extended condition, from a retracted position, thus causing the formation of cavity 910 in tissue 906. Because accessing device 900 is urged against tissue 906 in a perpendicular manner, distal end 904 of accessing device 900 develops a seal for sealing in later delivered drug into cavity 910. FIG. 9c depicts accessing device 900 without force contact transducer 902. FIG. 9c suggests how a non-perpendicular orientation of accessing device 900 with—respect to tissue 906 could result in seepage of delivered drug 912 from cavity 910. FIG. 9d further depicts accessing device 900 without force contact transducer 902 urged against tissue 900. Tissue 900 is further depicted in two states, diastolic state tissue 906a and systolic state tissue 906b correlating to the movement of myocardial tissue in a beating heart. As shown in FIG. 9d, diastolic position tissue 906a provides a seal between tissue 906 and accessing device 900. However, upon systolic movement, tissue 906 moves away from accessing device 900 unless sufficient contact force exists between accessing device 900 and tissue 906. Force contact transducer 902 provides information to the user to enable the user to apply sufficient and perpendicular force to the accessing device to create a seal between accessing device 900 and tissue 906 during the movements of beating heart between tissue 900a and 900b states. Moreover, FIG. 9d depicts how delivered drug 912 may be further ejected or pumped out of cavity 910 by the contractile actions between heart tissue 900a and 900b states.

Figure 10A:
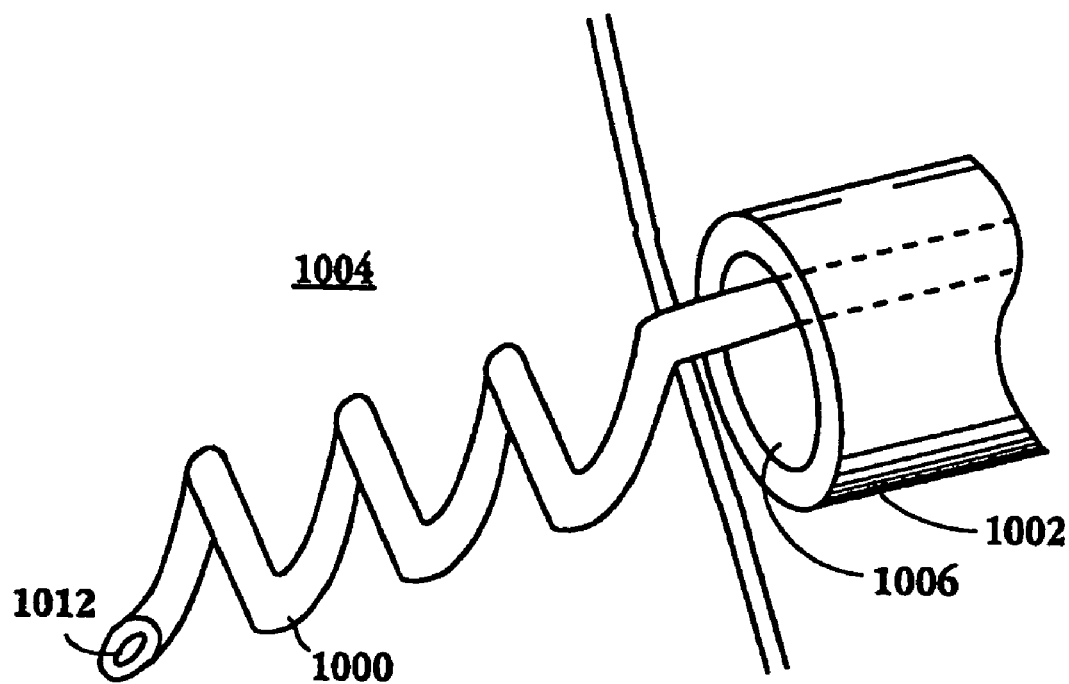
FIGS. 10 (a–b) depict a corkscrew shaped expandable member embodiment.
Figure 10B:
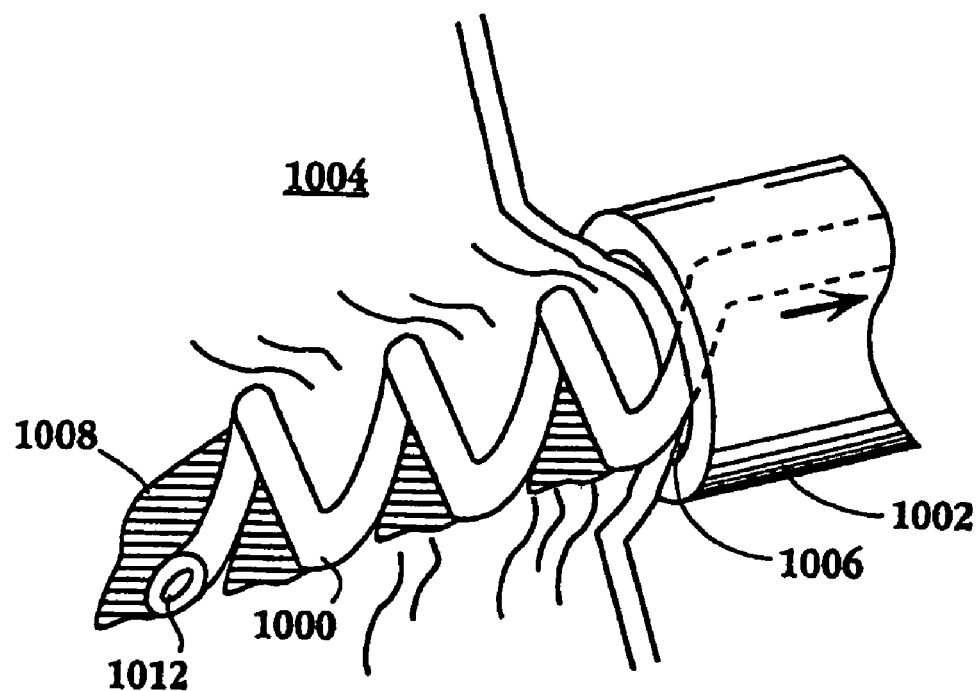

FIG. 10 depicts another embodiment of the invention utilizing corkscrew shaped tissue-penetrating implement 1000. Accessing device 1002 houses tissue-penetrating implement 1000 that may be rotated within accessing device in either a retracted condition or an extended condition. FIG. 10a depicts tissue-penetrating implement 1000 secured into tissue 1004 by screwing. As tissue-penetrating implement 1000 is withdrawn back towards a retracted condition, tissue 1004 is likewise pulled into lumen 1006 of accessing device 1002 thus creating seal 1006 between accessing device 1002 and tissue 1004. Such pulling further creates cavity 1008 at distal end 1010 of tissue-penetrating implement 1000. Cavity 1008 may then be filled with delivered-drug, not shown, delivered through lumen orifice 1012 to treat the walls of cavity 1008 with such drug.

Figure 11A:
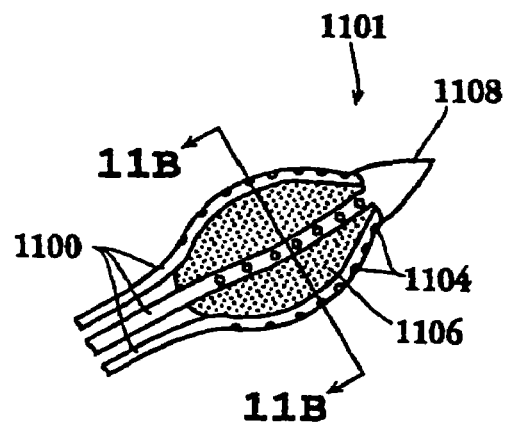
FIGS. 11 (a–c) depict a balloon expandable member embodiment.
Figure 11B:
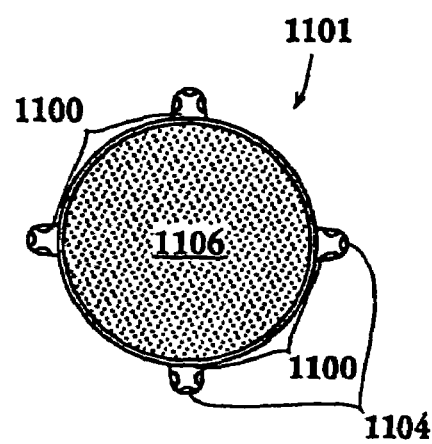
Figure 11C:
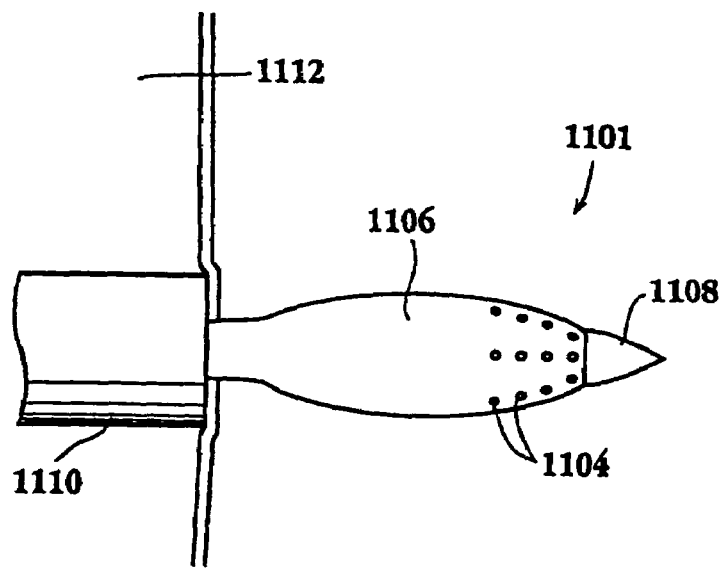

FIG. 11 depicts another embodiment of the invention where the expandable members comprise a balloon structure with drug-delivery lumen orifices distributed along the surface of the expandable members. FIGS. 11a and 11b depicts a tissue-penetrating implement 1101 comprising four radially distributed expandable members 1100 defining lumens 1102 with exit ports 1104 outwardly situated on balloon 1106. Penetrating tip 1108 is situated on the end of the balloon distal from accessing device 1110, not shown. As balloon 1106 is inflated, expandable members 1100 are urged outward against the tissue of a cavity, not shown. FIG. 11c further shows yet another embodiment using a balloon as an expandable member and drug-delivery channel. Accessing tool 1110 is urged against tissue 1112, whereby tissue-penetrating implement 1101 comprises a balloon expandable member 1106 with distally situated exit ports 1104 and penetrating or cutting tip 1108.

Figure 12A:
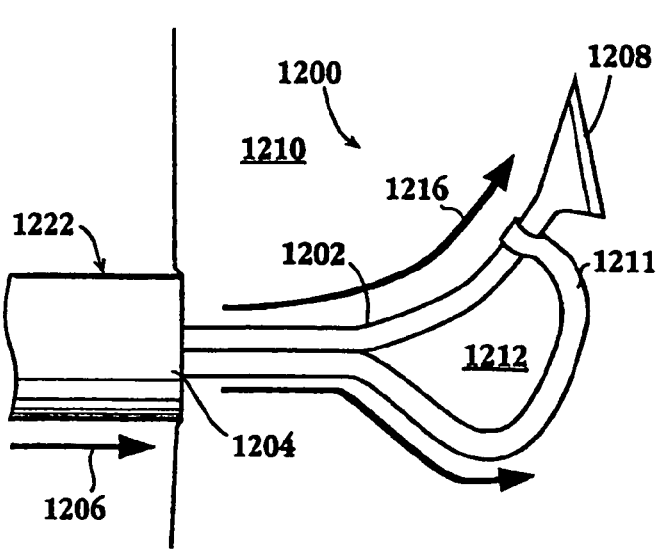
FIGS. 12 (a–c) depict an arc cutting embodiment.
Figure 12B:
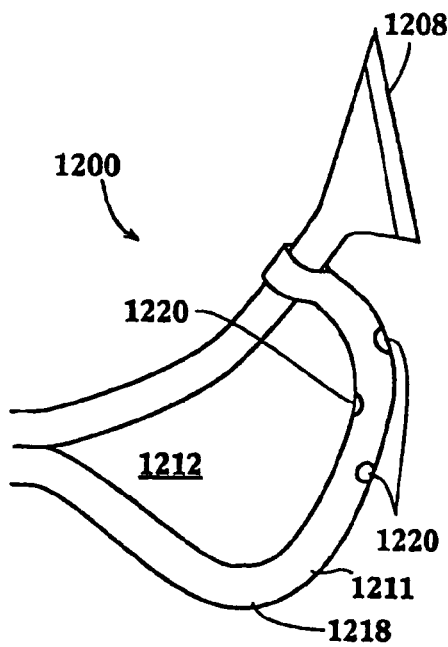

FIG. 12 depicts a preferred embodiment of the invention where tissue penetrating implement 1200 comprises at least one first expandable member 1202 made from a shape memory material composition having a first remembered arc shape and a second, stress induced, straight shape. First expandable member 1202 assumes a stress induced straight shape when housed within lumen 1204 of accessing tool 1206, but returns to its remembered shape upon extension beyond lumen 1204. As first expandable member 1202 extends from lumen 1202, it cuts an arc shaped path through tissue 1210 as first expandable member 1202 regains its remembered shape. Tissue-penetrating implement 1200 has cutting tip 1208 situated distal to accessing tool 1206 for cutting tissue 1210 as tissue-penetrating implement 1200 is advanced into tissue 1210 when advanced from a retracted condition to an extended condition out of lumen 1204. Second expandable member 1211 extends from lumen 1204 coaxial to first expandable member 1202. Adjacent tissue-penetration implement's distal end, first and second expandable members are positioned together either fixedly or slidably. When fixedly positioned, both expandable members 1202 and 1211 extend together, but expand longitudinally from one another to form cavity 1212. When first and second expandable members 1202 and 1211 are slidably positioned, the user may either extend one expandable member, preferably the first expandable member 1202 having cutting tip 1208, and then extend second expandable member 1211 to follow along cut path 1216 created by previously extended first expandable member 1202, expanding longitudinally away from first expandable member 1202 to create cavity 1212 where a drug may be infused from a drug-delivery reservoir, not shown, in fluid communication through a conduit with the distal region of accessing device 1222. FIG. 12b depicts a variation where second expandable member further comprises construction from shape memory tube 1218, such as nitinol or NiTi tubing, defining a longitudinal lumen in fluid communication with a drug-delivery reservoir, not shown, and terminating with exit ports 1220 adjacent to the distal end of second expandable member. During or after the formation of cavity 1212, drug may be delivered from the drug-delivery reservoir, not shown, to the cavity 1212 through the lumen and exit ports 1220 of second expandable member 1211.

Figure 12C:
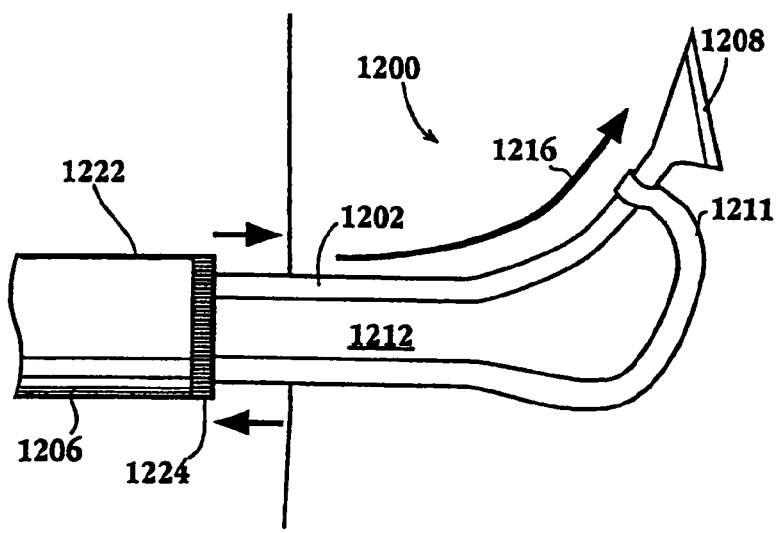

FIG. 12c depicts a variation where first and second expandable members 1202 and 1211 are spaced-apart from one another by, for example, having two lumens, not shown, defined within accessing device 1222. Force contact transducer 1224 is located on the distal end of accessing device 1222 to assist a user in achieving the sufficient and perpendicular contact force with respect to tissue 1210 to create a seal between tissue 1210 and the distal end of accessing device 1222. One skilled in the art would readily recognize the benefits of the above mentioned embodiment. In particular, the presence of second expandable member 1211 made from a shape memory material that assumes a stress induced straight shape when housed within lumen 1204 of accessing tool 1206, but returns to its remembered shape upon extension beyond lumen 1204, when configured as shown in FIG. 12, provides the ability to shepherd first expandable member 1202 further in its arc shape cutting path by applying lateral force to cutting tip 1208 as it cuts through tissue 1210. This further prevents cutting tip from accidentally cutting too deep through a wall like tissue and thus perforating the wall and turning a cavity into a passage.

Additional pharmaceutical methods may be employed to control the duration of action. Controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another method to control the duration of action by controlled release preparations is to incorporate the agent into particles of a polymeric material such as polyesters, polyamino acids, hydrogels, poly(lactic acid) or ethylene vinyl acetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin microcapsules and poly(methylrnethacylate) microcapsules, respectively, or in colloidal drug delivery systems, for example, liposomes, albumin microspheres, microemulsions, nanoparticles, and nanocapsules or in macroemulsions.

The drug-delivery tool and method of the present invention may employ a wide variety of agents, for example, ranging from active compounds to markers to gene therapy compounds. Exemplary agents, contemplated for use herein, are set forth in U.S. Pat. Nos. 5,840,059; 5,861,397; 5,846,946; 5,703,055; 5,693,622; 5,589,466; and 5,580,859, each expressly incorporated herein by reference. In one embodiment, for example, the invention is employed to deliver one or more genes (for example, as so-called "naked DNA") into cavities formed in the myocardium of a subject.

In appropriate situations, the agent can be delivered in a form that keeps the agent associated with the target tissue for a useful period of time, such as with a viscosity-enhancer to produce a thixotropic gel. In certain embodiments, the therapeutic or diagnostic agent is mixed with a viscous biocompatible polyol to maintain prolonged, high concentration of the agent in the channels and affect the kinetics of the agent-target region interaction.

Alternatively, a catheter could be employed to deliver an agent incorporated in a biocompatible polymer matrix. Suitable polymeric materials are known in the art, for example, as set forth in U.S. Pat. No. 5,840,059, incorporated herein by reference. For example, non-biodegradable polymers can be employed as hollow reservoirs or other structures. Additionally, conventional pharmacologically inert fillers may be employed to tailor the time release characteristics of the agent. Certain embodiments contemplate the use of biodegradable polymers, such as collagen, polylactic-polyglycolic acid, and polyanhydride. For example, the agent can be dispersed in a polymer which is configured to degrade over a useful period of time, releasing the agent. In one embodiment, the agent is released by swelling and sloughing of the biodegradable polymer. Various means for employing polymer compounds to secure a therapeutic agent are disclosed, for example, in Levy et al., WO 94/21237 and in U.S. application Ser. No. 08/033,307, filed Mar. 15, 1993, which is hereby incorporated by reference. In still other embodiments, a biocompatible material is delivered to seal and retain the agent within the cavity. For example, a delivery lumen could be employed to deliver a sealing agent after delivery of the agent.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims. For example, the expandable members of the tissue-penetrating implement can be configured not to expand, but rather to maintain a substantially constant configuration as it is moved between its retracted and advanced conditions. By this construction, the cage or skeleton structure defined by the expandable members can serve, when inserted into a tissue, to help form a temporary cavity, and maintain the cavity as one or more selected agents are delivered and/or drawn therein. Thus, while an expandable member (as described above) is advantageous for many purposes, a non-expandable cage or skeleton in place of the previously described expandable member can provide useful advantages, as well.

The invention claimed is:

1. A method for delivering a selected diagnostic or therapeutic agent to a target site within a selected body tissue having a surface, comprising the steps of:
    (a) providing a drug-delivery tool comprising
        (i) an accessing device having distal and proximal ends, an inner lumen extending therebetween, a drug-delivery reservoir, and a user-control structure;

(ii) a tissue-penetrating implement carried on the distal end of the accessing device for axial movement in and out of the lumen, wherein the implement comprises a tip for penetrating the body tissue, and is operatively connected to the user-control structure; and (iii) at least a first transducer located at the distal end of the accessing device;

(b) placing the distal end of the accessing device into contact with a selected body tissue surface;

(c) manipulating the orientation of the accessing device to a desired orientation, based on at least one signal from the first transducer;

(d) applying pressure to the selected body tissue surface with the distal end of the accessing device to create a seal;

(e) selectively actuating the tissue-penetrating implement to penetrate the selected body tissue surface; and (f) delivering a drug while maintaining the seal.

2. The method of claim 1, wherein the desired orientation comprises placing the distal end of the accessing device substantially perpendicular to the selected body tissue surface.

3. The method of claim 1, wherein the distal end of the accessing tool is substantially circular and has a circumference, and wherein the first transducer is situated on the circumference of the distal end.

4. The method of claim 3, wherein the first transducer is in the shape of an annular ring.

5. The method of claim 3, wherein the tissue-penetrating implement is in fluid communication with the drug-delivery reservoir, and is configured to release the drug after penetrating a selected body tissue surface.

6. The method of claim 5, wherein the selected body tissue is a heart tissue, and wherein natural movements in the heart tissue can cause a drug to be released by the tissue-penetrating implement.

7. The method of claim 5, wherein the tissue-penetrating implement further comprises a cavity configured to store the drug.

8. The method of claim 5, wherein the tissue-penetrating implement does not receive a drug from the drug-delivery reservoir until after the completion of step (e).

9. The method of claim 1, wherein the tissue-penetrating implement in steps (b) and (c) is retracted within the lumen so that no portion of the tissue-penetrating implement extends beyond the distal end of the accessing device.

10. The method of claim 1, wherein the tissue-penetrating implement is configured to store the drug.

11. The method of claim 1, wherein the drug-delivery tool further comprises a second transducer.

12. The method of claim 1, wherein the first transducer is a pressure transducer.

13. The method of claim 1, wherein the first transducer is an ultrasound transducer.

14. A method for delivering a selected diagnostic or therapeutic agent to a target site within a selected body tissue having a surface, comprising the steps of:

(a) providing a drug-delivery tool comprising
(i) an accessing device having distal and proximal ends, an inner lumen extending therebetween, a drug-delivery reservoir, and a user-control structure;
(ii) a tissue-penetrating implement carried on the distal end of the accessing device and operatively connected to the user-control structure; and
(iii) at least a first transducer located at the distal end of the accessing device;

(b) placing the distal end of the accessing device into contact with a selected body tissue surface;

(c) manipulating the orientation of the accessing device to a desired orientation, based on at least one signal from the first transducer;

(d) applying pressure to the selected body tissue surface with the distal end of the accessing device to create a seal when the body tissue is in a diastolic state; and (e) maintaining the seal while the body tissue is in a systolic state.

15. The method of claim 14, wherein a drug is released during the movement of the tissue between the diastolic state and the systolic state.

16. The method of claim 15, wherein the release of the drug is caused by the movement of the tissue from a diastolic state to a systolic state.

17. The method of claim 14, further comprising the step of selectively actuating the tissue-penetrating implement to penetrate the selected body tissue surface after step (d).

* * * * *